United States Patent [19]
Boni et al.

[11] Patent Number: 5,683,715
[45] Date of Patent: Nov. 4, 1997

[54] TAXANE-CONTAINING PHOSPHATIDYLCHOLINE LIPOSOMES

[75] Inventors: Lawrence Boni, Monmouth Junction, N.J.; Joel Portnoff, Langhorne, Pa.

[73] Assignee: The Liposome Company, Inc., Princeton, N.J.

[21] Appl. No.: 482,359

[22] Filed: Jun. 7, 1995

Related U.S. Application Data

[63] Continuation-in-part of Ser. No. 63,131, May 17, 1993, abandoned.

[51] Int. Cl.[6] .................................................. A61K 9/127
[52] U.S. Cl. ................................................................ 424/450
[58] Field of Search ........................... 424/450; 436/829; 428/402.2

[56] References Cited

U.S. PATENT DOCUMENTS

| | | | |
|---|---|---|---|
| 4,485,054 | 11/1984 | Mezei | 264/4.6 |
| 4,522,803 | 6/1985 | Lenk et al. | 424/1.1 |
| 4,534,899 | 8/1985 | Sears | 260/403 |
| 4,588,708 | 5/1986 | Fountain et al. | 424/1.1 |
| 4,721,612 | 1/1988 | Janoff et al. | 424/1.1 |
| 4,880,635 | 11/1989 | Janoff | 424/450 |
| 4,906,477 | 3/1990 | Kurono | 424/450 |
| 4,921,706 | 5/1990 | Roberts | 424/450 |
| 4,975,282 | 12/1990 | Cullis et al. | 424/450 |
| 5,008,050 | 4/1991 | Cullis et al. | 264/4.3 |
| 5,030,453 | 7/1991 | Lenk et al. | 424/450 |
| 5,059,421 | 10/1991 | Loughrey et al. | 424/417 |
| 5,100,662 | 3/1992 | Bolcsak et al. | 424/88 |
| 5,169,637 | 12/1992 | Lenk et al. | 424/450 |

OTHER PUBLICATIONS

Bangham et al, "Diffusion of Univalent Ions across the Lamellae of Swollen Phospholipids", J. Mol. Biol, 13:238 (1965).

Borman, "Scientsts Mobilize to Increase Supply of anticancer Drug Taxol". Chemical and Engineering News, Sep. 2, 1991.

Cullis, et al., in: Liposomes, From Biophysics to/therapeutic, M.J. Ostro, ed., Marcel Dekker, pp. 39–72 (1987).

Donehower et al., "Phase I Trail of Taxol in Patients With Advanced Cancer", Cancer Treat. Rep. 72(12):1171–(1987).

Edgington. "Taxol, Out of the Woods", Biotechnology, 9:933 (1991).

*Primary Examiner*—Gollamudi S. Kishore
*Attorney, Agent, or Firm*—Kenneth B. Rubin

[57] ABSTRACT

Provided herein are liposomal taxane formulations where the liposomal lipid is a phosphatidylcholine; these formulations are useful for treating animals afflicted with cancers.

15 Claims, 4 Drawing Sheets

TAXANE-CONTAINING PHOSPHATIDYLCHOLINE LIPOSOMES

This application is a continuation-in-part of Ser. No. 08/063,131 filed May 17, 1993, now abandoned.

FIELD OF THE INVENTION

This invention is directed to stable, therapeutically useful liposomal taxane formulations wherein the liposomal lipid is phosphatidylcholine.

Taxanes can be anticancer agents, which affect cell growth by blocking cell division. Paclitaxel (TAXOL®, Bristol-Myers Squibb), for example, is an antimitotic agent which binds to tubulin, thereby blocking the disassembly of microtubules and consequently, inhibiting cell division (Schiff et al., Nature 277:665 (1979)). The optimal effect of paclitaxel on polymerization and stabilization of microtubules is seen at concentrations near stoichiometric equivalence with tubulin dimers (Schiff and Horowitz, Proc. Natl. Acad. Sci. USA 77(3):1561–1565 (1980)). Paclitaxel has been found to have activity against ovarian and breast cancers, as well as against malignant melanoma, colon cancer, leukemias and lung cancer (see, e.g., Borman, Chemical & Engineering News, Sep. 2, 1991, pp. 11–18; The Pharmacological Basis of Therapeutics *** (Goodman Gilman et al., eds.)****, Pergamon Press, New York (1990), p. 1239; Suffness, Antitumor Alkaloids, in: "The Alkaloids, Vol. XXV," Academic Press, Inc. (1985), Chapter 1, pp. 6–18; Rizzo et al., J. Pharm. & Biomed. Anal. 8(2):159–164 (1990); and Biotechnology 9:933–938 (October, 1991).

Paclitaxel can be isolated from natural sources, or prepared synthetically from naturally occurring precursors, e.g., baccatin, by attachment of protecting groups to the hydroxyl groups of these precursors that are to become the hydroxyl groups of paclitaxel, converting the precursors, and then removing the protecting groups from the hydroxyl groups to obtain paclitaxel (see, e.g., WO93/10076, int. pub. date May 27, 1993; K. V. Rao, U.S. Pat. No. 5,200,534; R. A. Holton, U.S. Pat. No. 5,015,744; PCT/U.S.92/07990; V. J. Stella and A. E. Mathew, U.S. Pat. No. 4,960,790; K. C. Nicolaou, Nature 364 (1993), pp. 464–466; Nicolaou, K. C. et al. Nature 367 (1994) pp.630–634; Holton, R. A., et al. J. Am. Chem. Soc. 116 (1994) pp. 1597–1600; WO93/16059, int. pub. date Aug. 19, 1993; EP 528,729, published Feb. 24, 1993; EP 522,958, published Jan. 13, 1993; WO91/13053, int. pub. date Sep. 05, 1991; EP 414,610, int. pub. date Feb. 27, 1991).

Paclitaxel is highly insoluble in water and aqueous solvents, and is currently supplied as an emulsion in a polyoxyethylated derivative of castor oil and ethanol (CremophorEL)®. However, administration of this formulation generally entails premedication with other drugs and a slow infusion of a large volume, to avoid toxicity associated with the Cremophor vehicle. Patients are therefore generally required to be admitted to hospitals over night. Compositions provided herein comprising a liposomal taxane solve this problem, by providing a formulation in which the taxane remains stably associated with the liposome during storage, but which avoid the premedication and admittance problems.

SUMMARY OF THE INVENTION

This invention provides a liposome comprising a taxane and a bilayer comprising a lipid, wherein the lipid consists essentially of a phosphatidylcholine. Typically, the concentration of the taxane is at least about one mole percent, preferably from about 1 mole percent to about 4 mole percent. The taxane can be paclitaxel, taxotere, a baccatin or a cephalomannine, and is preferably paclitaxel. Preferably, the taxane is associated with the liposomal bilayer. The phosphatidylcholine (PC) is an unsaturated or partially unsaturated PC and includes, without limitation, dioleoyl phosphatidylcholine (DOPC), palmitoyloleoyl phosphatidylcholine (POPC), or egg phosphatidylcholine (EPC); preferably, the PC is EPC. Preferably, the liposome is unilamellar, more preferably a unilamellar liposome having an average diameter of from about 100 nm to about 200 nm. The liposome can be dehydrated.

Also provided is a pharmaceutical composition comprising a pharmaceutically acceptable carrier and the liposome. Further provided is a method of administering a taxane to an animal, preferably a human, which comprises administering to the animal this pharmaceutical composition. This method can be used to administer liposomal taxanes to animals afflicted with cancers, e.g., brain, breast, colon, liver, lung, ovarian or prostate cancer; such therapeutic use requires administration of an anticancer effective amount of the taxane. Preferably, the taxane administered is paclitaxel. Typically, the anticancer effective amount of the taxane is generally at least about 0.1 mg of the taxane per kg of body weight of the animal; desirably, the anticancer effective amount of the taxane is from about 1 mg per kg to about 500 mg per kg.

Still further provided herein is a liposome composition comprising: (I) a dehydrated liposome which comprises a taxane and a bilayer comprising a lipid; and (ii) one or more protective sugars at the inside and outside surfaces of the bilayer, wherein the lipid consists essentially of a phosphatidylcholine.

DETAILED DESCRIPTION OF THE INVENTION

Figure 1:
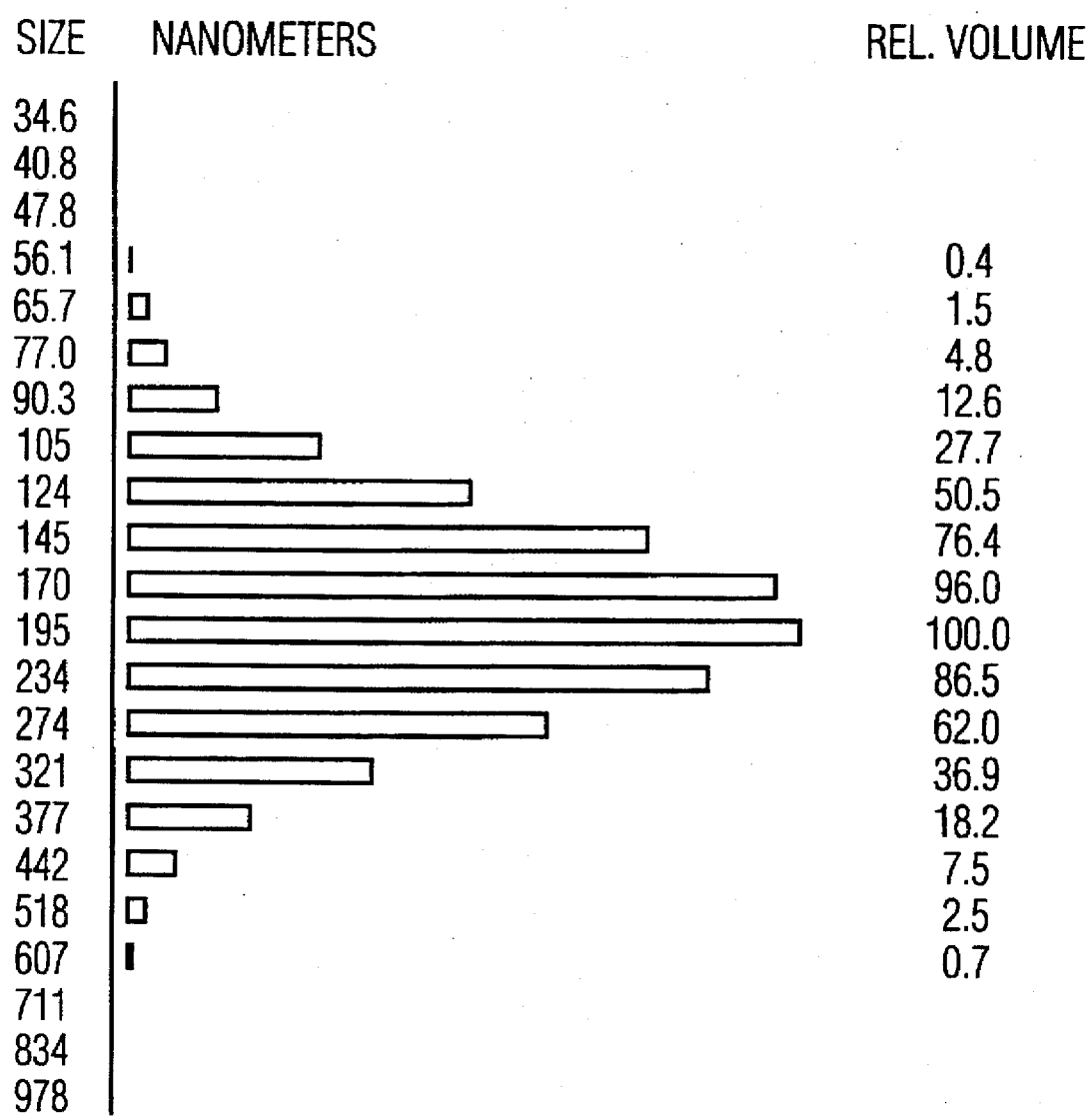
FIG. 1. Gaussian analysis of the size distribution of EPC multilamellar liposomes having substantially equal interlamellar solute distribution (no paclitaxel). Run time: 5 min, 39 sec; average count rate: 340.3 kHz; channel width: 21.0 μsec; temp.: 23 deg. C.; viscosity: 0.9325 centipoise; index of refraction: 1.333; print AT data: 500 kcounts; number of printouts: 10. Mean diameter: 204.5 nm; standard deviation: 75.1 nm (26.8%); chi squared: 0.2; baseline adjust: 0.00%; data: 508.2 k.

This invention provides a liposome comprising a taxane and a bilayer comprising a lipid, wherein the lipid consists essentially of a phosphatidylcholine. Typically, the concentration of the taxane is at least about one mole percent, preferably from about 1 mole percent to about 4 mole percent. However, the concentration may be higher or lower as needed. The lower concentration limit is governed by the least amount of paclitaxel it is practical to make liposomes with given the intended use of the liposomal paclitaxel, and may be readily determined by ordinarily skilled artisans. The upper limit is governed by the paclitaxel crystallization concentration, i.e., the concentration at which it separates out from lipid bilayers and forms aggregates.

Taxanes have the general formula:

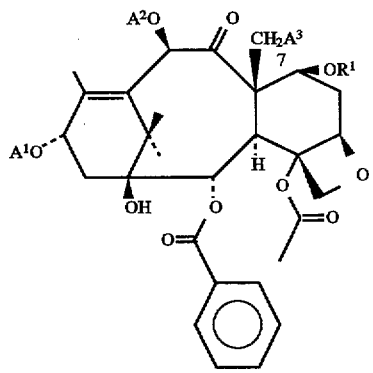

Paclitaxel ([Compound I]) is the preferred taxane herein ($A^1$: $C_6H_5C(O)NHCH(C_6H_5)CH(OR)C(O)$—; $A^2$:$CH_3C(O)$—; A3: H). However, taxotere (II), which differs from paclitaxel by having a tert-butoxy carbonyl group at the C-12 position, instead of a benzoyl group, and a hydroxyl group, instead of an acetyloxy group, at C-10 is also useful herein. Accordingly, for taxotere, $A^1$ is $(CH_3)_3COC(O)NHCH(C_6H_5)CH(OR)(O)$—, $A^2$ is H, and $A^3$ is H. Cephalomannine (III), differs from paclitaxel in the amide group located at the distal end of the C-13 ester. $A^1$ is then $(CH_3)CH=O(CH_3)C(O)NHCH(C_6H_5)CH(OR)C(O)$—, $A^2$ is $CH_3C(O)$— and $A^3$ is H. Additional taxanes useful in accordance with the practice of this invention include, without limitation: 19-hydroxybaccatin III [IV], Baccatin V [V], 10-deacetyl cephalomannine [VI], 10-deacetyl paclitaxel [VII], 7-Epi-10-deacetyl paclitaxel [VIII], 7-Epi-10-deacetyl cephalomannine [IX], and 10-deacetyl baccatin III [X], as described in the following table, in addition to paclitaxel, taxotere and cephalomannine. Preferably, the taxane is associated with the liposome's lipid bilayer.

| Compound | $A^1$ | $A^2$ | $A^3$ |
|---|---|---|---|
| Paclitaxel (I) | $C_6H_5C(O)NHCH(C_6H_5)CH(OR)C(O)$— | $CH_3C(O)$— | H |
| Taxotere (II) | $C(CH_3)_3OC(O)NHCH(C_6H_5)CH(OR)C(O)$— | H | H |
| Cephalo-mannine (III) | $(CH_3)CH=C(CH_3)C(O)NHCH(C_6H_5)CH(OR)C(O)$— | $CH_3C(O)$— | H |
| 19-hydroxy baccatin III (IV) | H | $CH_3C(O)$— | OH |
| Baccatin III (V) | H | $CH_3C(O)$— | H |
| 10-Deacetyl cephalo mannine (VI) | $(CH_3)CH=C(CH_3)C(O)NHCH(C_6H_5)CH(OR)C(O)$— | H | H |
| 10-Deacetyl paclitaxel (VII) (7α-OH) | $C_6H_5C(O)NHCH(C_6H_5)CH(OR)C(O)$— | H | H |
| 7-Epi-10 deacetyl paclitaxel (VIII) (7β-OH) | $C_6H_5C(O)NHCH(C_6H_5)CH(OR)C(O)$— | H | H |
| 7-Epi-10-deacetyl cephalo mannine(7β-OH) (IX) | $(CH_3)CH=C(CH_3)C(O)NHCH(C_6H_5)CH(OR)C(O)$— | H | H |
| 10-Deacetyl baccatin III (X) | H | H | H |

Phosphatidylcholines (PCs) are preferred herein for liposome formulation with taxanes. PCs having unsaturated acyl chains, that is fatty acids having one or mor double bonds between adjacent carbon atoms, or partially unsaturated acyl chains, that is, one unsaturated and one saturated, are preferred herein. These unmsaturated or partially unsaturated PCs include, withjout limitation, dioleoyl phosphatidylcholine (DOPC), palmitoyloleoyl phosphatidylcholine (POPC), or egg phosphatidylcholine (EPC).

Such lipids are the most effective at inhibiting taxane crystallization and concomittant precipitation from lipid bilayers, as demonstrated by the crystallization data presented below (see Example 1). Dispersion of paclitaxel and a lipid were formulated, with the paclitaxel and lipid concentrations (as well as the relative proportions of paclitaxel and lipid) given in Table 1 (see below). The ability of paclitaxel to form a stable dispersion with a lipid, described in the table as a "Yes", indicates that the lipid can be a suitable liposome-based carrier for the taxane, that is, liposomal taxane formulations will be stable in storage. Stable liposomal taxane preparations are generally characterized by an absence of taxane aggregation and crystallization. Preferred lipids are those a unit weight of which a greater amount of a taxane can be associated with; that is, the paclitaxel/lipid ratios and mole percent paclitaxel in the dispersion are highest for the preferred lipids; consequently, the lipid/paclitaxel ratio is lower in the preferred lipids. The data presented in Table 1 claerly show that the paclitaxel/lipid ratio and mole percent paclitaxel in the dispersion are highest (43.99 micrograms/milligram and 3.76, respectively) for the most preferred PC, that is, EPC.

Liposomes are spontaneously self-assembling structures comprising one or more bilayers of amphipathic lipid molecules enclosing an internal aqueous volume. The amphipathic lipid molecules which make up lipid bilayers comprise a polar (hydrophilic) headgroup region covalently linked to one or more non-polar (hydrophobic) acyl chains. The energetically unfavorable contact between the hydrophobic acyl chains and the aqueous medium causes the molecules to rearrange such that the polar headgroups are facing the aqueous medium internal or external to the liposome, while the acyl chains reorient towards the bilayer interior. The net result is an energetically stable structure in which the acyl chains are effectively shielded from coming into contact with the aqueous medium.

Liposomes can be unilamellar, that is, have a single lipid bilayer, or multilamellar, having multiple lipid bilayers, and can have diameters ranging from about 25 nm to several microns. Multilamellar liposomes (MLVs) comprise a plurality of lipid bilayers each of which encloses an aqueous compartment; preferred MLVs have aqueous compartments comprising a solute, wherein the concentration of the solute in each of the aqueous compartments is substantially equal, i.e., the liposome has substantially equal interlamellar solute distribution. Preferably, the liposome of this invention is unilamellar, more preferably a unilamellar liposome having an average diameter of from about 100 nm to about 200 nm. For example, this unilamellar liposome can be a $LUVET_{100}$ or $LUVET_{200}$, i.e., a unilamellar liposome produced by extrusion of multilamellar liposome through filters with pore sizes of 100 nm or 200 nm, respectively (see Cullis et al., U.S. Pat. No. 5,008,050, the contents of which are incorporated herein by reference).

The liposome of this invention can be dehydrated, stored and then reconstituted such that a substantial portion of their internal contents are retained in the liposomes. Liposomes are preferably dehydrated using standard equipment or equivalent apparatii; preferably, dehydrated liposmes are freeze-dried under reduced pressure. Alternatively, liposomes can also be dehydrated without prior freezing, by placing the liposomes under reduced pressure. Dehydration without prior freezing typically takes a longer period of time than does dehydration-freezing, but is generally believed to have less potential to damage liposome structure than does dehydration with prior freezing.

Liposomal dehydration generally requires use of a hydrophilic drying protectant (see U.S. Pat. No. 4,880,635, the contents of which are incorporated herein by reference). This hydrophilic compound is generally believed to prevent the rearrangement of the lipids in the liposome, so that the size and contents are maintained during the drying procedure and through rehydration, such that the liposomes can be reconstituted. Appropriate qualities for such drying protectants are that they be strong hydrogen bond formers, and possess stereochemical features that preserve the intramolecular spacing of the liposome bilayer components. Saccharide sugars, preferentially mono- and disaccharides, more preferably, disaccharides, are suitable drying protectants for liposomes. Alternatively, the drying protectant can be omitted if the liposome preparation is not frozen prior to dehydration, and sufficient water remains in the preparation subsequent to dehydration and if the liposome is multilamellar. Preferably, the protective sugar concentration in the liposome composition prior to dehydration is from about 100 mM to about 250 mM, or from about 5 moles of sugar per mole of phosphatidylcholine to about 12.5 moles of sugar per mole phosphatidylcholine. The protective sugar should be present at both inside and outside the liposome bilayers prior to dehydration. Without intending to be limited by theory, it is generally believed that protective sugars inside liposome bilayers prior to dehydration inhibit leakage of liposome contents, and that outisde sugars inhibit interliposomal aggregation and fusion. Further provided herein is a liposome composition comprising: (I) a dehydrated liposome which comprises a taxane and a bilayer comprising a lipid; and (ii) one or more protective sugars at the inside and outside surfaces of the bilayer, wherein the lipid consists essentially of a phosphatidylcholine A variety of methods exist for producing liposomes (for a review, see, e.g., Szoka and Paphadjopoulos, in: *Liposomes: From Physical Structure to Therapeutic Applications* (C. G. Knight, ed., Elsevier/North Holland, pp. 51–82 (1981); Cullis et al., in: *Liposomes, From Biophysics to Therapeutics* M. J. Ostro, ed.), Marcel Dekker, pp. 39–72 (1987)). Bangham's original preparation (J. Mol. Biol. 13:238 (1965)) involves suspending phospholipids in an organic solution and then evaporating the solution to dryness, leaving a phospholipid film on the walls of the reaction vessel. Next, an appropriate amount of a chosen aqueous medium is added; the resulting liposomes, which consist of multilamellar vesicles (MLVs), are dispersed by mechanical means. This technique provided the basis for the development of sonicated unilamellar vesicles by Paphadjopoulos et al. (Biochem. Biophys. Acta. 135:624 (1968)), Lenk et al. (U.S. Pat. Nos. 4,522,803, 5,030,453 and 5,169,637) and Fountain et al. (U.S. Pat. No. 4,588,708) disclose methods for producing multilamellar liposomes with substantially equal interlamellar solute distribution. FATMLVs, freeze-and-thaw multilamellar vesicles, also have substantially equal interlamellar solute distribution (Cullis et al., U.S. Pat. No. 4,975,282). These vesicles are produced by first dispersing a lipid in an aqueous solvent to form multilamellar liposomes. The resulting lipid vesicles are rapidly frozen, the frozen mixture is warmed, and then the freeze-thaw cycle is repeated at least three times. Furthermore, Janoff et al. (U.S. Pat. No. 4,721,612) and Bolcsak et al. (U.S. Pat. No. 5,100,662) describe the preparation of liposomes of enhanced stability using sterols. Cullis et al. (U.S. Pat. No. 5,008,050) and Loughrey et al. (U.S. Pat. No. 5,059,421 ) disclose the preparation of a population of liposomes with a defined size distribution by extrusion of liposomes through filters under pressure. The contents of these patents are incorporated herein by reference.

Bioactive molecules entrapped within liposomes can have an enhanced therapeutic index and improved biodistribution. Liposomal drugs are gradually released in the circulation, thereby alleviating the toxic side effects associated with administration of the free drug and minimizing the amount of the drug that need be administered to maintain desired serum levels. Additionally, liposomal drug administration can raise the maximum amount of a drug that can safely be administerted. Furthermore, drug-lipid formulations may be directed to intracellular sites of infection.

Also provided is a pharmaceutical composition comprising a pharmaceutically acceptable carrier and the liposome. For the purposes of this invention, a "pharmaceutically acceptable carrier" means any of the standard carriers, diluents, excipients and the like generally intended for use in connection with the administration of biologically active agents to animals. Such carriers are well known in the art and are generally chosen with regards to a number of factors, such as the particular drug being used and the intended route of administration, which are understood by the ordinarily skilled artisan. Pharmaceutical carriers preferred for use in accordance with the practice of this invention are those well known carriers suitable for use in connection with intravenous administration of liposomes and include, but are not limited to, sterile aqueous solutions such as physiological saline, 5% dextrose USP solutions and various aqueous buffers, e.g., aqueous phosphate buffers. The total solute concentration in such carriers should be controlled to keep the composition isotonic. Pharmaceutically acceptable carriers may also contain additional components, such as antioxidants, preservatives and the like, which are compatible with the active agent. The choice of such additional components is well within the purview of the ordinarily skilled artisan. Other carriers, e.g., tablets for oral administration and oils for mucosal or topical administration, may be prepared employing general knowledge and used in accordance with the practice of this invention.

Still further provided is a method of administering a taxane to an animal, preferably a human, which comprises administering to the animal this pharmaceutical composition. This method can be used to administer liposomal taxanes to animals afflicted with cancers, e.g., brain, breast, colon, liver, lung, ovarian or prostate cancer; such therapeutic use requires administration of an amount of the pharmaceutical composition which comprises an amount of the liposome comprising an anticancer effective amount of the taxane. Preferably, the taxane administered is paclitaxel.

For the purposes of this invention, an "effective anticancer amount" is any amount of the liposome effective to treat a cancer, e.g., by inhibiting the growth of tumors or proliferation or metastasis of cancer cells. This amount will generally depend upon specific factors relevant to individual cases. Such factors are well known to ordinarily skilled artisans, or may readily be determined by them without undue experimentation. They include, but are not limited to: the type of cancer being treated and the stage of its progression; the type of animal being treated, as well as its age, weight and general condition; the particular drug being used, and whether it is being used in combination with other drugs; the type of liposome employed and the drug-to-lipid ratio in the liposome. Typically, the anticancer effective amount of the taxane is at least about 0.1 mg of the taxane per kg of body weight of the animal; desirably, the anticancer effective amount of the taxane is from about 1 mg per kg to about 500 mg per kg.

Cancers which may be treated with the liposomes of this invention include, but are not limited to: brain, breast, ovarian, lung, and colon cancers or malignant melanomas. Paclitaxel, because of its antimitotic activity and its ability to inhibit cell migration, is a valuable treatment for tumors, which exhibit more rapid cell division than normal tissues. Taxane activity against ovarian, lung, brain, breast and other types of tumors has been documented (see, e.g., Borman, Chemical and Engineering News, Sep. 2, 1991; Edgerton, Biotechnology, 9:933 (1991); The Pharmacological Basis of Therapeutics (Goodman Gilman et al., eds.), Pergamon Press, New York (1990); Rizzo et al., J. Pharm. & Biomed. Anal. 8(2):159 (1990); Donehower et al., Cancer Treat. Rep. 71(12):1171 (1987) Grem et al., Cancer Treat. Rep. 71(12):1179; Wiernik et al., J. Clin. Oncol. 5(8):1232 (1987), the contents of which are incorporated herein by reference). In a presently preferred embodiment of this invention, the liposomal formulations provided herein are used in the treatment of animals afflicted with ovarian cancer.

This invention will be better understood from the examples which follow. However, those of ordinary skill in the art will readily understand that these examples are merely illustrative of the invention as defined in the claims which follow thereafter.

EXAMPLES

Example 1
Paclitaxel/Lipid Association

Dispersion of paclitaxel and a lipid were formulated, with the paclitaxel and lipid concentrations (as well as the relative proportions of paclitaxel and lipid) given in Table 1 (see below). The ability of paclitaxel to form stable dispersions with each lipid is indicated (a "Yes" in Table 1 indicates that a stable dispersion was formed.

TABLE 1

PACLITAXEL ASSOCIATION WITH VARIOUS LIPIDS

PART A

| Lipid | Paclitaxel Dispersion | Paclitaxel (mg/ml) | Lipid (mM) | Paclitaxel/ Lipid (µg/mg) | Lipid/ Paclitaxel (m/m) | Mole % |
|---|---|---|---|---|---|---|
| DMPC | Yes | 0.5846 | 27.9 | 30.91 | 40.8 | 2.39 |
| DPPC | Yes | 0.4585 | 15.9 | 39.3 | 29.7 | 3.26 |
| DSPC | Yes | 0.6190 | 22.6 | 34.66 | 31.2 | 3.11 |
| DMPG | Yes | 0.7107 | 29.7 | 34.73 | 35.7 | 2.72 |
| POPG | Yes | 0.7222 | 27.1 | 34.31 | 32.0 | 3.03 |
| SOPC | Yes | 0.6878 | 27.3 | 34.8 | 32.3 | 3 |
| DOPC | Yes | 0.7107 | 35.2 | 25.68 | 42.3 | 2.31 |
| DEPC | Yes | 0.6534 | 26.8 | 31.01 | 35.1 | 2.77 |
| BPS:EPC (1:3, w/w) | Yes | 0.8024 | 26.0 | 39.94 | 27.7 | 3.48 |
| EPC | Yes | 0.8024 | 24.0 | 43.99 | 25.6 | 3.76 |
| CHS | Yes | 0.7680 | N/A | 38.4 | N/A | N/A |
| THS | No | N/A | N/A | N/A | N/A | N/A |
| MOPE | Micellar | 0.182 | N/A | 9.1 | N/A | N/A |
| DPhytPC | Yes | 0.6763 | 23.7 | 33.7 | 29.90 | 3.24 |
| DLPE | Poorly hydrated | 0.5732 | 24.9 | 25.18 | 37.1 | 2.62 |
| DOPE | No | N/A | N/A | N/A | N/A | N/A |

Part B

| 24 hours | Crystals in 5 Days | Crystals in 7 Months | Crystals in |
|---|---|---|---|
| DMPC | Yes | N/A | N/A |
| DPPC | Yes | N/A | N/A |
| DSPC | Yes | N/A | N/A |
| DMPG | Yes | N/A | N/A |
| POPG | Yes | N/A | N/A |
| SOPC | No | No | Yes |
| POPC | No | No | Yes |
| DOPC | No | Yes (tubules) | N/A |
| DEPC | No | Yes | N/A |
| BSP:EPC (1:3, w/w) | ? | Yes | N/A |
| EPC | No | No | Yes |
| CHS | No | Yes | N/A |
| THS | N/A | N/A | N/A |
| MOPE | No | No | Yes |
| DPhytPC | No | No | Yes |
| DLPE | No | Yes | N/A |
| DOPE | N/A | N/A | N/A |

DMPC: dimyristoyl phosphatidylcholine; DPPC: dipalmitoyl phosphatidylcholine; DSPC: distearoyl phosphatidylcholine; DMPG: dimyristoyl phosphatidylglycerol; POPG: palmitoyloleoyl phosphatidylglycerol; SOPC: stearoyloleoyl phosphatidylcholine; DOPC: dioleoyl phosphatidylcholine; DEPC: dielaidoyl phosphatidylcholine; BSP/EPC: brain sphingomyelin/egg phosphatidylcholine; CHS: cholesterol hemisuccinate; THS: tocopherol hemisuccinate; MOPE: mono-oleoyl phospahtidylethanolamine; DPhytPC: diph ytanolyl phosphatidylcholine; DLPE: dilauroyl phosphatidylethanolamine; DOPE: dioleoyl phosphatidylethanolamine.

The initial screening of lipid candidates was performed at a target paclitaxel concentration of 30 micrograms paclitaxel per milligram lipid, using a target lipid concentration of 20 milligrams per milliliter. The actual lipid concentration was determined for phospholipids by using a modified Bartlett assay. Paclitaxel concentration was determined by UV absorbance, using the standard literature value of 29,800 liter $mol^{-1}$ $cm^{-1}$ at 228 nm for the molar extinction coefficient. In cases where lipid absorbed appreciably, a correction was made by subtracting the lipid contribution to the absorbance at that wavelength. Physical stability of the preparations were examined by light microscopy to determine the presence of paclitaxel crystals, which appeared as needle-shaped aggregates

Example 2

Formation of Egg Phosphatidylcholine Multilamellar Liposomes (MLVs) Containing Paclitaxel Solutions of egg phosphatidylcholine (EPC) and paclitaxel were formed by dissolving EPC/paclitaxel mixtures (100 mg EPC and 3 mg paclitaxel) in 1.5 ml of chloroform or methylene chloride. Addition of sodium carbonate aqueous buffer (5 ml) solution, with stirring, following organic solvent removal resulted in the formation of multilamellar liposomes. No crystallization of paclitaxel was observed either by light or electron microscopy and no paclitaxel pellet was seen upon centrifugation in histopaque. However, small rectangular paclitaxel crystals, which precipitate upon centrifugation in histopaque (50% dilution), were observed when these multilamellar liposomes were sonicated.

Example 3

Formation of Egg Phosphatidylcholine/Paclitaxel Liposomes Having Substantially Equal Interlamellar Solute Distribution Liposomes were formed by dissolving a mixture of 100 mg of EPC and 3 mg of paclitaxel in 1.5 ml methylene chloride, adding 5 ml of sodium carbonate buffer and emulsifying the buffer while evaporating the methylene chloride, with a nitrogen stream, according to the procedure described in Lenk et al. (U.S. Pat. Nos. 4,522,803, 5,030,453 and 5,169,637). No crystallization of paclitaxel was observed in these formulations.

Example 4

Formation of Egg Phosphatidylcholine/Paclitaxel Liposomes Having Substantially Equal Interlamellar Solute Distribution Liposomes containing EPC, but no paclitaxel (placebo vesicles), were formed with 10 grams of EPC and 75 ml of methylene chloride according to the above-described procedure (see Example 3). The EPC and methylene chloride were mixed with an A-200 propeller (high shear). The mean diameter (see FIG. 1) of the liposomes formed, as determined by NICOMP, was 204.5 nm. Freeze-fracture electron microscopy showed liposomes with diameters of from about 65 nm to about 350 nm, in agreement with the NICOMP.

Figure 2:
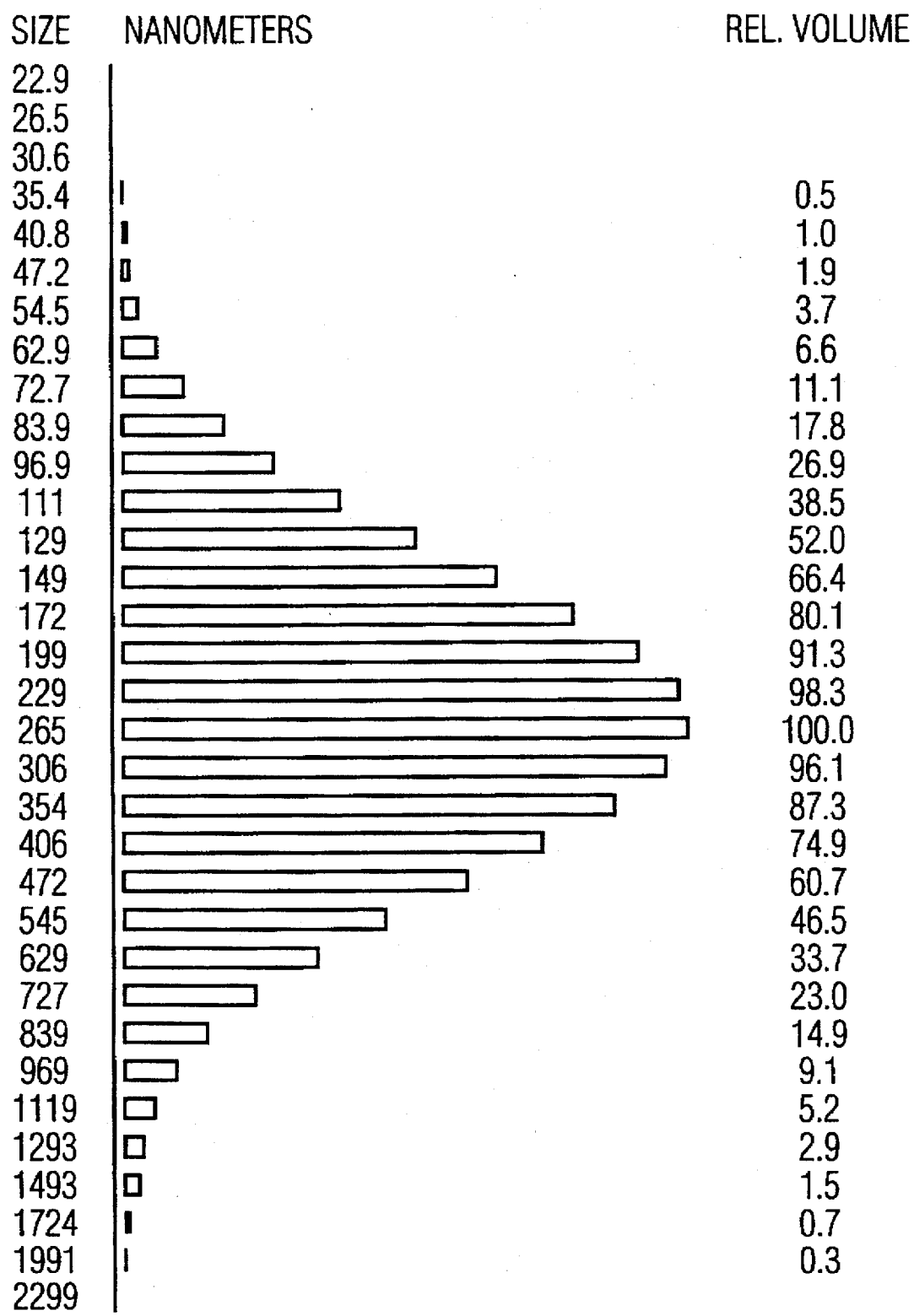
FIG. 2. Gaussian analysis of the size distribution of EPC SPLVs containing paclitaxel. Run time: 6 min, 25 sec; average count rate: 345.5 kHz; channel width: 26.0 μsec; temp.: 23 deg. C.; viscosity: 0.9325 centipoise; index of refraction: 1.333; print AT data: 500 kcounts; number of printouts: 10. Mean diameter: 209.8 nm; standard deviation: 187.2 nm (60.4%); chi squared: 4.8; baseline adjust: 0.01%; data: 698.4 k.
Figure 3:
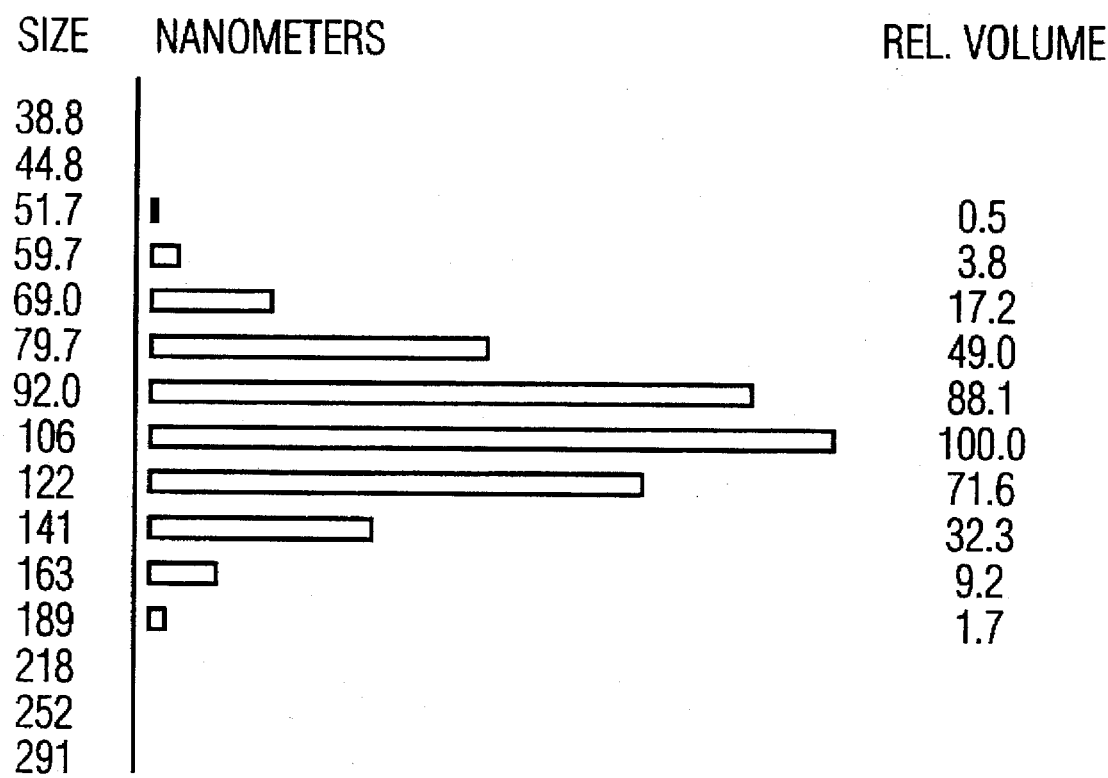
FIG. 3. Gaussian analysis of the size distribution of EPC/paclitaxel unilamellar liposomes produced by extrusion of SPLVs through polycarbonate filters with 0.1 micron pores (LUVET 100s). Run time: 8 min, 42 sec; average count rate: 356.5 kHz; channel width: 12.0 μsec; temp.: 23 deg. C.; viscosity: 0.9325 centipoise; index of refraction: 1.333; print AT data; 500 knouts; number of printouts: 10. Mean diameter: 105.2 nm; standard deviation: 22.3 nm (21.2%); chi squared: 0.3; baseline adjust: 0.08%; data: 503.6 k.
Figure 4:
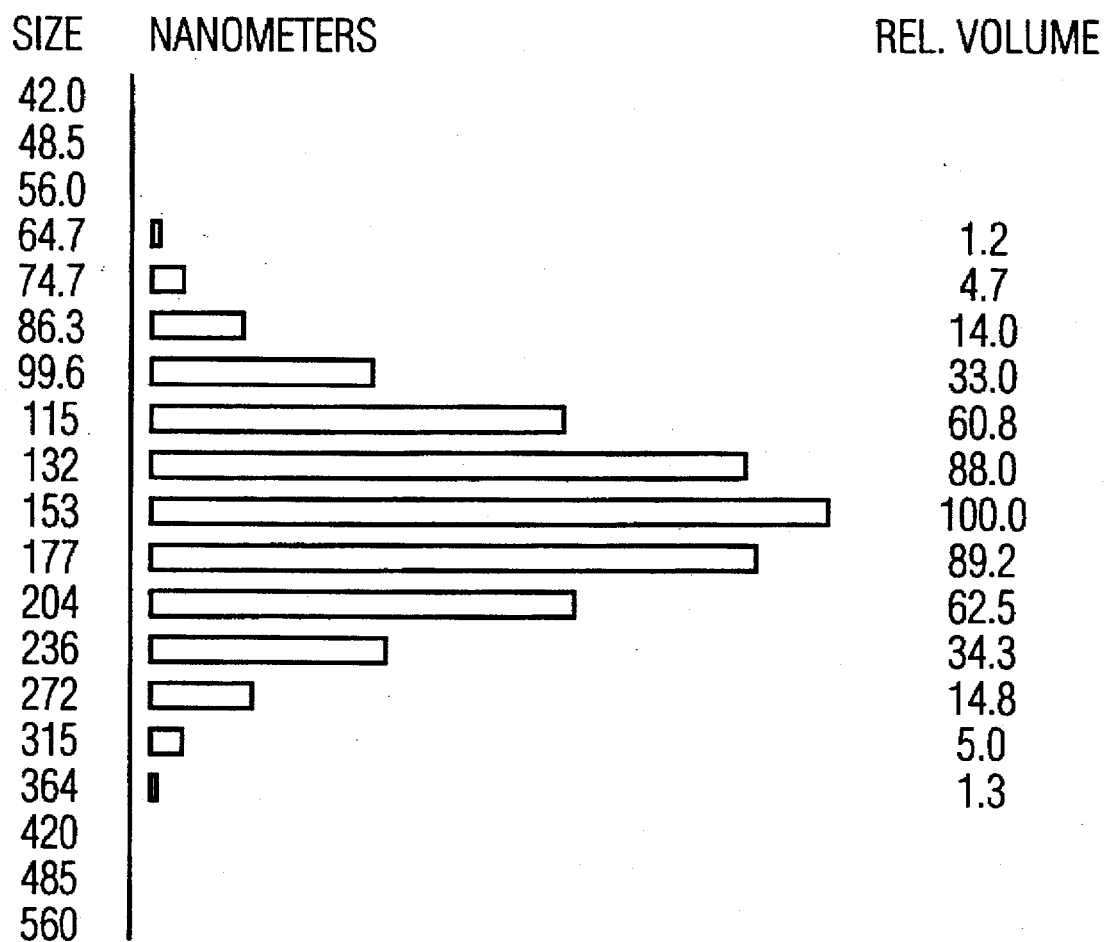
FIG. 4. Gaussian analysis of the size distribution of EPC/paclitaxel unilamellar liposomes produced by extrusion of SPLVs through polycarbonate filters with 0.2 micron pores (LUVET 200s). Run time: 8 min, 42 sec; average count rate: 345.9 kHz; channel width: 16.0 μsec; temp.: 23 deg. C.; viscosity: 0.9325 centipoise; index of refraction: 1.333; print AT data: 500 kcounts; number of printouts: 10. Mean diameter: 160.8 nm; standard deviation: 47.0 nm (29.2%); chi squared: 0.3; baseline adjust: 0.00%; data: 624.8 k.

Liposomes containing EPC and paclitaxel were formed using 10 grams of EPC, 300 mg of paclitaxel and 75 ml of methylene chloride by the same procedure. The mean diameter of the liposomes formed, as determined by NICOMP, was 309.8 nm (see FIG. 2). Freeze-fracture electron microscopy showed that vesicles with diameters of from about 90 to about 1200 nm were formed. The EM studies also showed that the interlamellar spacings in these liposomes were large and irregular, which is indicative of a repulsion between the layers. No paclitaxel crystallization was observed by light or EM microscopy or upon centrifugation in histopaque. Crystals 5 to 15 microns long were observed, by light microscopy, after the liposomes had been stored for about one week in the cold room (4 deg. C.) These were removed by centrifugation in histopaque, saving the supernatants and discarding the resulting pellets.

Example 5

Preparation of EPC/Paclitaxel Unilamellar Liposomes

Multilamellar liposomes containing EPC and paclitaxel (MW 853.9) were prepared as described above (see Example 3). The MLVs were then extruded through 0.1 micron and 0.2 micron Nucleopore™ polycarbonate filters. Paclitaxel concentrations were determined by spectrophotometry using an extinction coefficient of $\theta = 29,700$ L/mol.cm$^{-1}$ at 229 nm. Due to the overlap with the EPC peak, subtraction of this peak was performed by using an equivalent amount of EPC in the reference cell. Five percent of the paclitaxel contained within the EPC MLVs was lost after the multiple extrusions through the 0.2 micron filters. Nine percent was lost after extrusion through the 0.1 micron filters. No paclitaxel crystallization was observed in any of the unilamellar liposomes produced by the extrusion process.

Example 6

Efficacy Data

Liposomes containing egg phosphatidylcholine (EPC) and paclitaxel were made, as described above, and then administered (intravenously, day 1) to groups of mice in the doses indicated below. The number of mice in each group surviving until the end of the observation period (15 days) was then determined.

| Toxicity of EPC-Paclitaxel Liposomes in Normol Mice (non-tumor) | | |
|---|---|---|
| Treatment | Dose mg/kg | # Mice dead/Total Mice |
| Paclitaxel: cremophor | 10.4 | 0/5 |
|  | 20.7 | 0/5 |
|  | 41.5 | 2/5 |
|  | 83.0 | 5/5 |
| Paclitaxel-Liposomes | 10.4 | 0/5 |
|  | 20.7 | 0/5 |
|  | 41.5 | 1/5 |
|  | 83.0 | 4/5 |

The LD50, that is, the dose giving 50.% lethality, for paclitaxel:cremophor was 46 mg/kg, and that for paclitaxel-liposomes was 57 mg/kg.

| Effect of EPC - Paclitaxel Liposomes on Survival of Mice Bearing L1210 Tumor | | | |
|---|---|---|---|
| | Dose mg/kg | Median Survival (days) | % ILS* |
| Controls | — | 9.0 | — |
| Paclitaxel: cremophor | 5 | 10.0 | 11 |
|  | 10 | 8.5 | −6 |
|  | 20 | 10.0 | 11 |
|  | 30 | 10.0 | 11 |
| Paclitaxel-Liposomes | 5 | 8.0 | −11 |
|  | 10 | 9.5 | 6 |
|  | 20 | 10.0 | 11 |
|  | 30 | 9.0 | 0 |

*ILS = increase in median survival as % of control survival; mice injected i.p. with $10^5$ L1210 cells day 0; treatment given I.V. × 1 on day 1.

| Effect of EPC - Paclitaxel Liposomes on Survival of Mice Bearing B16 Melanoma | | | |
|---|---|---|---|
| Treatment | Dose mg/kg* | Median Day of Death | % ILS |
| Controls | — | 19.0 | — |
| Paclitaxel: cremphor | 6.25 | 25.0 | 32 |
|  | 12.5 | 28.0 | 47 |
|  | 25.0 | 30.0 | 58 |
| Paclitaxel-Liposomes | 6.25 | 27.5 | 45 |
|  | 12.5 | 32.5 | 71 |
|  | 25.0 | 38.5 | 103 |
|  | 50.0 | 35.0 | 84 |
|  | 100.0 | 10.0 | −45 |

ILS = increase in median survival as % of control survival; 3 doses given every 4 days starting day 1, i.p.; mice injected i.p. with 0.5 ml of 10% B16 melanoma cells brei, day 0.

What is claimed is:

1. A liposome consisting essentially of a lipid and paclitaxel, wherein the lipid is an unsaturated or a partially unsaturated phosphatidylcholine.

2. The liposome of claim 1, wherein the concentration of paclitaxel is at least about one mole percent.

3. The liposome of claim 2, wherein the concentration of paclitaxel is from about 1 mole percent to about 4 mole percent.

4. The liposome of claim 1, wherein paclitaxel is associated with the bilayer.

5. The liposome of claim 1 wherein the phosphatidylcholine is dioleoyl phosphatidylcholine, palmitoyloleoyl phosphatidylcholine, or egg phosphatidylcholine.

6. The liposome of claim 5, wherein the phosphatidylcholine is egg phosphatidylcholine.

7. The liposome of claim 1 which is dehydrated.

8. A pharmaceutical composition comprising a pharmaceutically acceptable carrier and the liposome of claim 1.

9. A method of administering paclitaxel to an animal which comprises administering to the animal the pharmaceutical composition of claim 8.

10. The method of claim 9, wherein the animal is a human.

11. The method of claim 9, wherein the animal is afflicted with a cancer and wherein the pharmaceutical composition comprises an anticancer effective amount of paclitaxel.

12. The method of claim 11, wherein the cancer is a brain, breast, colon, liver, lung, ovarian or prostate cancer.

13. The method of claim 11, wherein the anticancer effective amount is at least about 0.1 mg of paclitaxel per kg of body weight of the animal.

14. The method of claim 11, wherein the anticancer effective amount is from about 1 mg of paclitaxel per kg to about 500 mg per kg.

15. A liposome composition which comprises: (i) a dehydrated liposome consisting essentially of paclitaxel and a lipid; and (ii) one or more protective sugars at the inside and outside surfaces of the bilayer, wherein the lipid is an unsaturated or partially unsaturated phosphatidylcholine.

* * * * *